United States Patent [19]

Niles et al.

[11] Patent Number: 5,594,116
[45] Date of Patent: Jan. 14, 1997

[54] TRYPTASE POLYCLONAL ANTIBODY AND PURIFICATION METHOD FOR USE IN HUMAN TRYPTASE IMMUNOASSAY

[75] Inventors: Andrew L. Niles; Mary Haak-Frendscho, both of Madison, Wis.

[73] Assignee: Promega Corporation, Madison, Wis.

[21] Appl. No.: 555,130

[22] Filed: Nov. 8, 1995

[51] Int. Cl.$^6$ .............................. A23J 1/00; C07K 1/00; C07K 14/00; C07K 16/00
[52] U.S. Cl. ................ 530/413; 424/130.1; 424/124; 210/635; 210/656; 422/70; 435/803; 435/6; 435/2; 530/412; 530/417; 585/825
[58] Field of Search ................ 530/413, 412, 530/417; 435/6, 2; 514/12; 424/130.1, 124; 210/635, 656; 422/70; 585/825

[56] References Cited

U.S. PATENT DOCUMENTS

| | | | |
|---|---|---|---|
| 4,752,563 | 6/1988 | Kortright et al. | 435/2 |
| 5,049,502 | 9/1991 | Humphries | 435/240.2 |
| 5,202,253 | 4/1993 | Esmon et al. | 435/240.27 |
| 5,449,610 | 9/1995 | Lillehoj | 435/7.24 |
| 5,476,839 | 12/1995 | Scott et al. | 514/12 |
| 5,500,344 | 3/1996 | Sayers et al. | 435/6 |

OTHER PUBLICATIONS

Gassman, M et al, Schweiz Arch Tierheilkd, 1990, 132(6) pp. 289–94 (abstract).
Braganza et al, Biochemistry, 1991, 30, pp. 4997–5007.
Tribbick et al, J Immun. Methods, 139(1991) 155–166.
Tsang et al, J Immun. Methods, 138(1991) pp. 291–299.
Bauwens et al, Clinica Chimica Acta, 170, (1987) pp. 37–44.
Castells et al, J Immun., vol. 138, (7), Apr. 1, 1987, pp. 2184–2189.
Mendelson et al, Arch. Biochem Biophys, 243(2) Dec., 1985, pp. 480–491.
Wenzel, S., et al., (1986), "Immunoassay of Tryptase from Human Mast Cells," *Journal of Immunological Methods*, 86:139–142.
Schwartz, L. B., et al., T., (1987a), "Tryptase Levels as an Indicator of Mast–Cell Activation in Systemic Anaphylaxis and Mastocytosis," *The New England Journal of Medicine*, 316:1622–1626.
Schwartz, L. B., et al., (1987b), "Quantitation of Histamine, Tryptase, and Chymase in Dispersed Human T and TC Mast Cells," *The Journal of Immunology*, 138:2611–2615, No. 8.
Schwartz, L. B., et al., (1994), "Development of a New, More Sensitive Immunoassay for Human Tryptase: Use in Systemic Anaphylaxis", *Journal of Clinical Immunology*, 14:190–204.
Schwartz, L. B., (1995), "Structure and Function of Human Mast Cell Tryptase," Biological and Molecular Aspects of Mast Cell and Basophil Differentiation and Function, Chapter 14:161–173, Raven Press, Ltd: New York.
Scopes, R. K., (1994), "Protein Purification, Principles and Practice," Springer–Verlag: New York.

Walls, A. F., et al., (1990a), "Production and Characterization of Monoclonal Antibodies Specific for Human Mast Cell Tryptase," *Clinical and Experimental Allergy*, 20:581–589.
Walls, A. F., et al., (1990b), "Immunohistochemical Identification of Mast Cells in Formaldehyde–Fixed Tissue Using Monoclonal Anitbodies Specific for Tryptase," *Journal of Pathology*, 162:119–126.
Walls, A. F., et al., (1991), "Mast Cell Tryptase and Histamine Concentrations in Bronchoalveolar Lavage Fluid from Patients with Interstitial Lung Disease," *Clinical Science*, 81:183–188.
Watkins, J., et al., (1993), "Improved Diagnosis of Anaphylactoid Reactions by Measurement of Serum Tryptase and Urinary Methylhistamine," *Ann Fr Anesth Rèanim.*, 12:169–172.
Lavery, J. P. and Lisse, J. R., (1994), "Preliminary Study of the Tryptase Levels in the Synovial Fluid of Patients with Inflammatory Arthritis," *Annals of Allergy*, 72:425–427.
Little, S. S. and Johnson, D. A., (1995), "Human Mast Cell Tryptase Isoforms: Separation and Examination of Substrate–Specificity Differences," *Biochem J.*, 307:341–346.
Livingston et al., (1975), *Methods in Enzymology*, 34:723–731.
Niles, A. L., et al., (1995), "Mast Cell Secretagogues in Bladder Inflammation," 9th International Congress of Immunology, Promega Corporation.
Nilsson, G. and Schwartz, L. B., (1994), "Mast–Cell Heterogeneity: Structure and Mediators," Blackwell Scientific Publications, Boston, pp. 195–208.
Ohtsuka, T., et al., (1993), "Time Course of Plasma Histamine and Tryptase Following Food Challenges in Children With Suspected Food Allergy," *Annals of Allergy*, 71:139–146, No. 2.
Pharmacia Tryptase RIACT Article.
Platt, M. S., et al., (1994), "Involvement of Mast Cells in Sudden Infant Death Syndrome," *J. Allergy Clin. Immunol.*, 94:250–256.
Rasp, G. and Hochstrasser, K., (1993), "Tryptase in Nasal Fluid is a Useful Marker of Allergic Rhinitis," *Allergy*, 48:72–74.
Sant, G. R. and Theoharides, T., (1994), "The Role of the Mast Cell in Interstitial Cystitis," *Urologic Clinics of North America*, 31:41–53.
Schneider, E., et al., (1992), "Determination of Human Mast Cell Tryptase by Bioluminescence–Enhanced Two–Site Immunometric Assay," *Eur. J. Clin. Chem. Clin. Biochem.*, 30:871–873.

(List continued on next page.)

*Primary Examiner*—James C. Housel
*Assistant Examiner*—Ginny Allen Portner
*Attorney, Agent, or Firm*—DeWitt Ross & Stevens SC

[57] ABSTRACT

The disclosure describes highly specific tryptase polyclonal antibodies, and a method to purify the antibodies. Specifically, the invention relates to polyclonal antibodies which have the capacity to capture tryptase out of solution, a process to generate the antibodies, and an enzyme-linked immunosorbent assay (ELISA) for human tryptase which utilizes the antibodies.

10 Claims, 7 Drawing Sheets

OTHER PUBLICATIONS

Amon, U., et al, (1993), "Investigations on Plasma Levels of Mast Cell Mediators in Acute Atopic Dermatitis," *Journal of Dermatological Science*, 7:63–67.

Beyer, K., et al., (1994), "Serum Tryptase and Urinary 1–Methylhistamine as Parameters for Monitoring Oral Food Challenges in Children," *Int Arch Allergy Immunol.*, 104:348–351.

Hattori, T., et al., (1989), "Involvement of Tryptase–Related Cellular Protease(s) in Human Immunodeficiency Virus Type 1 Infection," Elsevier Science Publishers B.V. (Biomedical Division), 248:48–52, No. 1,2.

Johnston, S. L., et al., (1993), "The Effect of Local Hyperthermia on Allergen–Induced Nasal Congestion and Mediator Release," *J. Allergy Clin. Immunol.*, 92:850–856.

Lavens, S. E., et al., (1993), "A Sensitive Colorimetric Assay for the Release of Tryptase from Human Lung Mast Cells In Vitro," *Journal of Immunological Methods*, 166:93–102.

TRYPTASE POLYCLONAL ANTIBODY AND PURIFICATION METHOD FOR USE IN HUMAN TRYPTASE IMMUNOASSAY

FIELD OF THE INVENTION

The present invention relates to highly specific tryptase polyclonal antibodies, and a method to purify the antibodies. More specifically, the present invention relates to polyclonal antibodies which have the capacity to capture tryptase out of solution, a process to generate the antibodies, and enzyme-linked immunosorbent assays (ELISA) for human tryptase which utilize the antibodies.

BIBLIOGRAPHY

Complete bibliographic citations to the non-patent references cited herein can be found in the Bibliography section, immediately preceding the claims.

DESCRIPTION OF THE PRIOR ART

Mast Cells and Tryptase Release

In order to comprehend the unique sensitivity and specificity of the present immunoassay, some background information regarding human mast cells is in order. Mast cells are granulated, immunologically activatable cells which are positioned in various tissues throughout the body. Mast cells are found in large numbers in tissues at potential entry points of noxious substances. For instance, mast cells are abundant in the skin, the conjunctiva, the gut, and the lungs. Mast cells also are present, in more modest numbers, in the liver, kidney, and adrenals.

In humans, mast cells have a mean diameter of approximately 10 μm. The most striking morphologic feature of mast cells are granules which constitute approximately fifty percent of the total cell volume. Mature mast cells also have nuclei which lack deeply divided lobes.

Several different nomenclatures are currently in use for describing particular types of mast cells. However, none of the nomenclature systems is optimal because they do not necessarily relate to putative functional differences between the cells. For instance, rodent mast cells are often referred to as either mucosal or connective, depending on their origin. These terms, however, imply that mast cell differences are determined by where the cell is found, which is inaccurate. Identical mast cells in rodents may be found in both mucosal and connective tissue sites.

In humans, perhaps the most useful nomenclature relates to the presence of chymase proteases within the granules of the mast cells. All granules of human mast cells contain histamine, tryptase, and heparin. A sub-population of human mast cells also contain chymase, carboxypeptidase, and a cathepsin G-like protease. Those mast cells which contain chymase are designated $MC_{TC}$, while those mast cells which do not contain chymase are designated $MC_T$. As used herein, the term "mast cell" or "MC," without further designation, shall refer to any and all types of mast cells, without limitation. Further clarification of these terms will be used where necessary.

$MC_T$ cells are the most predominant, but not the exclusive, type of mast cell found in the lungs and in the small intestine mucosa, while $MC_{TC}$ cells predominant in the skin and intestinal submucosa. The relative abundance of the two types of MC's may, however, change with tissue inflammation or fibrosis.

Upon immunologic activation, MC's degranulate and release pre-formed mediators including histamine, proteoglycans such as heparin, and proteinases including tryptase. The degranulation process begins essentially immediately upon activation, and ends within minutes.

The release of histamine from MC's is the major initiating event of the allergenic response. Within minutes of its release, cellular histamine is rapidly metabolized to either methylhistamine, methylimidazole acetic acid, or imidazole acetic acid. The extremely rapid metabolism of histamine makes it quite difficult to directly quantify histamine levels either in vivo or in vitro.

Simultaneously with the release of histamine, activation and degranulation of mast cells also results in the release of tryptase. Tryptase appears to account for about twenty percent of the entire protein content in a typical MC. Tryptase is released from MC's as a macromolecular protease-proteoglycan complex, in conjunction with heparin. Tryptase diffuses relatively slowly through tissues compared to histamine, presumably due to its association with the macromolecular proteoglycan complex.

A very important characteristic of tryptase is that it is virtually absent from any other type of cell. While negligible amounts have been measured in human basophils (0.04 pg/cell), Nilsson and Schwartz (1994), other cell types found in normal lung, skin, and bowel, as well as eosinophils, neutrophils, monocytes, and lymphocytes from peripheral blood all lack any detectable level of tryptase. Therefore, tryptase is an extremely discriminating marker of human mast cell degranulation. Sensitive quantitation of in vivo tryptase levels therefore may serve as an indicator of the extent of MC degranulation.

Tryptase

Tryptase itself is a tetrameric endoprotease of approximately 134 kDa. Each of the four subunits is approximately 31 to 34 kDa in size. Tryptase is a neutral, serine protease found exclusively in mast cell granules, as noted above. For a complete discussion regarding mast cell heterogeneity, structure, and mediators, see Nilsson and Schwartz (1994).

As noted in Schwartz (1995), human tryptase was first purified to apparent homogeneity from dispersed and enriched lung mast cells in 1981. However, further research has shown that there are at least two different types, or groups, of human tryptase. These tryptase isoforms are designated herein as α-tryptase and β-tryptase.

Little and Johnson (1995) describe the isolation and characterization of two forms of human lung mast cell tryptase, which they designate high-HLT (high-molecular-mass human lung tryptase, 33 kDa) and low-HLT (low-molecular-mass human lung tryptase, 29 kDa). These two tryptase isoforms were found to be immunologically cross reactive. It also was found that these two isoforms of human lung tryptase cleave the natural substrates HMMK and VIP in a different manner and at different rates.

Disease States Associated with Mast Cell Degranulation

In addition to a wide range of allergic responses, including allergic rhinitis (Rasp and Hochstrasser, 1991) and suspected food allergies (Beyer et al., 1994; Ohtsuka et al., 1993), elevated tryptase levels are associated with a diverse range of human disease states and conditions, including interstitial cystitis (Sant and Theoharides, 1994; Niles et al., 1995), acute atopic dermatitis (Amon et al., 1994), inflammatory arthritis (Lavery and Lisse, 1994), temperature-induced nasal congestion (Johnston et al., 1993), sudden infant death syndrome (Platt et al., 1994), HIV type I infection (Hattori et al., 1989) and anaphylactoid shock reactions (Watkins and Wild, 1994). It must be noted that tryptase is not a causative factor of the above conditions, rather that elevated tryptase levels often accompany such conditions.

More generally, mast cells play a critical role in inflammation by linking both the humoral and cellular immune systems. Both IgE and non-IgE mechanisms are known to cause mast cells to degranulate, thereby releasing tryptase into the extracellular milieu.

Clearly, in view of the large number of disease states in which MC degranulation and the release of tryptase has been implicated, there is a distinct need for a tryptase assay which is precise, accurate, sensitive, easy to use, and free of radioactive isotopes. Such an assay, which is the subject of the present invention, will shed new light on the role of mast cell degranulation and the effect of tryptase-mediated bio-reactions in human disease.

Prior Art Immunoassays for Human Tryptase

A number of different immunoassays, including a commercially available radioimmunoassay (RIA) and enzyme-linked immunosorbent assays (ELISA) using monoclonal antibodies, have been developed to assay for tryptase. Each of these techniques, however, has one or more negative features which mitigate against their widespread use or acceptance by researchers in the field.

Pharmacia (Uppsala, Sweden) markets an RIA specific for human tryptase under the trademark RIACT. This RIA utilizes iodine-labelled mouse monoclonal anti-tryptase antibodies. Briefly, RIA's are an analytical technique based upon an immunological reaction for measuring the presence and amount of proteins (e.g. antibodies, antigens, peptide hormones, enzymes, etc.). RIA's can be constructed in different configurations, their shared feature being that a radioactive label is used to follow the interaction of an antibody with an antigen. RIA's may be based on direct binding, i.e. by directly measuring the amount of radioactivity in an antibody-antigen precipitate. Indirect methods also may be employed. For instance, the RIA may be based upon the capacity of an unlabelled protein to compete with a known standard in binding to an antibody. The protein concentration of the sample is determined by comparing the degree of inhibition with that produced by a series of labelled standards containing known amounts of the protein being measured.

Because RIA's utilize an immunologic reaction, they are generally quite specific and sensitive. Pharmacia's literature states that the sensitivity limit of their RIACT radioimmunoassay system is 0.5 U/l (U/l is an equivalent expression for µg/l and ng/ml).

However, Beyer et al. (1994) and Ohtsuka et al. (1993) found the sensitivity limit of the RIACT radioimmunoassay system to be closer to 1.0 µg/l. Beyer et al. further noted that in their study of food challenges in children, while serum tryptase concentration appeared to be specific for marked clinical reaction after oral food challenges, the sensitivity of the RIACT radioimmunoassay system provided no better results than clinical evaluation. Beyer et al. suggest that a more sensitive assay might solve this problem. The same sentiment also is voiced by Amon et al (1994).

Watkins and Wild note that serum tryptase levels of normal individuals are extremely low, on average less than 1 ng/mg plasma. Moreover, factors including sepsis and myocardial infarction do not result in detectable rises in such small background levels of tryptase. Therefore, these authors suggest that the measurement of tryptase may be used to distinguish mast cell-dependent anaphylactoid responses from other systemic events, such as septic shock, cardiogenic shock, or vasovagal shock, which often present with identical manifestations. However, the ability to precisely and accurately measure tryptase serum levels is hampered by the sensitivity limits of the currently available RIA's such as the RIACT radioimmunoassay.

The radioactive label normally used in RIA's, and that used in the RIACT system, is $^{125}I$. More specifically, Pharmacia's RIACT system utilizes $^{125}I$-labelled mouse monoclonal anti-tryptase antibodies.

Unfortunately, like all assays utilizing radioactive isotopes, extreme care must be taken and special handling and storage equipment used in order to prevent radioactive contamination. As is stressed in all material handling guides, there is no minimum safe dose of ionizing radiation. When delivered from the factory, the standard reagents included in Pharmacia's RIACT radioimmunoassay emit 311 kBq (8.5 µCi) of radiation. This adds considerable expense to the use of RIA's in the form of increased equipment and disposal costs. It also makes use of RIA's inconvenient and inherently more dangerous than non-radioactive assay methods. Moreover, the kit must be used within weeks (i.e., it has a short shelf life) due to the short half-life of $^{125}I$.

The extra costs when using RIA's, including extra equipment costs and disposal costs, and the extreme inconvenience of using radioactive reagents, makes RIA's an increasingly unfavored assay method.

Schneider et al. (1992) describe a bioluminescence-enhanced two-site immunometric assay for human tryptase. This assay was reported to have a usable linear range of from 10 ng to 10 µg per liter. The assay is engineered around the release of D-luciferin from D-luciferyl-O-β-galactoside by the action of β-galactosidase, which is conjugated to anti-tryptase IgG. The luciferin generated is then reacted with a luciferase to generate photons which can be quantified using standard luminometers.

Lavens et al. (1993) describe a colorimetric assay for the in vitro release of tryptase from MC's. This assay is based upon tryptase cleaving a synthetic substrate, benzoyl-DL-arginine-p-nitroaniline, to liberate nitroaniline. The nitroaniline then is detected spectrophotometrically by measurement at 410 nm. A comparison of standardized tryptase levels as measured by the colorimetric assay and tryptase levels measured with the RIACT radioimmunoassay system showed that the two methods of measurement gave very similar results (r=0.92, P<0.01). Of particular relevance here, Lavans et al. note that the sensitivity limit of their colorimetric assay is only 10 ng/ml. Like Beyer et al. (1994) and Ohtsuka et al. (1993) above, Lavans et al. have found that in practice, commercially-available radioimmunoassays are considerably less sensitive than what is reported in the vendor's sales literature.

Still further tryptase assays, utilizing standard ELISA techniques have been developed using monoclonal antibodies for the capture and detect antibodies. In short, ELISA's generally utilize antigen-specific monoclonal antibodies in concert with a specific antibody-enzyme conjugate to detect and quantify proteins (e.g., immunoglobulins). The basic ELISA protocol can be modified to give different types of ELISA's, such as indirect, antibody-sandwich, and double antibody-sandwich ELISA's.

The basic protocol for a double antibody-sandwich ELISA is as follows: A plate is coated with antibodies (called capture antibodies) specific for the immunoglobulin being assayed. The plate is then washed with a blocking agent, such as bovine serum albumin (BSA) to block non-specific binding of immunoglobulins to the test plate. The test solution then is incubated on the plate coated with the capture antibodies. The plate then is washed, incubated with detect antibodies, washed again, and incubated with a specific antibody-enzyme conjugate. After incubation, the unbound conjugate is washed from the plate and enzyme substrate is added. The presence of the bound antibody-enzyme conjugate results in a proportional color change which can be measured and quantified.

For instance, Wenzel et al. (1986) describe an antibody-sandwich ELISA using a mouse monoclonal anti-tryptase antibody termed G5 in the solid phase and monospecific goat IgG anti-tryptase antibody together with tryptase in the fluid phase. The authors here report that this immunoassay is capable of quantifying between 0.1 ng to 5.6 ng of tryptase per 100 microliters (1 ng to 56 ng per milliliter) of sample solution, using standardized solutions. However, further researchers, Schwartz et al. (1987a), found this ELISA to lack sufficient sensitivity.

Schwartz et al. (1987a) used the ELISA of Wenzel et al., described immediately above, to analyze in vivo tryptase levels in patients having systemic mastocytosis, anaphylactic reactions, myocardial disease, and sepsis. In regard to the Wenzel et al. ELISA, Schwartz et al. note that one disadvantage of measuring tryptase using this ELISA is that the level of tryptase in control serum is normally below the limit of detection for the ELISA, which Schwartz et al. noted to be 2.5 ng per milliliter. Therefore, small elevations in tryptase could not be detected by the Wenzel et al. ELISA. Schwartz et al. note that neither sepsis nor myocardial infarction alone results in consistently detectable levels of tryptase in serum using the Wenzel et al. ELISA.

Schwartz et al. (1987b) used the same Wenzel et al. ELISA to assay the levels of tryptase from preparations of dispersed human $MC_{TC}$ cells obtained from foreskin and $MC_T$ cells obtained from lungs. Here, Schwartz et al. found that dispersed human lung mast cells were predominantly of the $MC_T$ phenotype, while dispersed adult and newborn foreskin mast cells were almost exclusively of the $MC_{TC}$ phenotype.

Walls et al. (1990a and 1990b) describe the production, characterization, and use in ELISA's of three monoclonal antibodies (mAbs) specific for human tryptase. Walls et al. (1990a) describe the initial production of the monoclonal antibodies, which are designated AA1, AA3, and AA5, as well as an indirect ELISA to detect tryptase. The monoclonal antibodies were produced using BALB/c mice by immunization on Day 0 with 0.25 mg tryptase in complete Freund's adjuvant, followed by boosters on Day 28 and Day 56 with 0.25 mg tryptase in incomplete Freund's adjuvant.

Three days after a final boost consisting of an intravenous injection of the mice with tryptase in saline (on Day 80), lymphocytes from two separate mouse spleens were fused with NS-1 (P3-N3-1/1-Ag 4.1) mouse myeloma line at a ratio of 2:1 using standard and well-known somatic cell fusion techniques. Cells were cloned and subcloned, and three cell lines secreting human tryptase-specific antibodies were identified using an indirect ELISA.

Here, a plate is coated with tryptase, non-specific binding blocked, and culture supernate added to the wells along with peroxidase-conjugated rabbit anti-mouse IgG. The color reaction then is developed with o-phenylene diamine hydrochloride, in standard fashion.

Crossed immunoelectrophoresis analysis of the mAbs using rabbit anti-tryptase serum revealed that all three monoclonal antibodies bound to the major immunoprecipitate. Using the indirect ELISA described above, Walls et al. found that the mAb designated AA5 had a consistently higher degree of binding to tryptase than did either the AA1 or AA3 mAbs.

Walls et al. (1990b) describe using the AA5 mAb discussed above for the immunohistochemical identification of mast cells in formaldehyde-fixed tissues. Here, an avidin-biotin enhanced immunoperoxidase procedure was used which resulted in intense staining of mast cells in paraffin-embedded tissues.

In a related procedure, Walls et al. (1991) describe an avidin-biotin enhanced antigen-capture ELISA utilizing polyclonal rabbit anti-tryptase antibodies, in combination with the mouse AA5 monoclonal antibodies described above. This ELISA was used to measure tryptase levels in bronchoalveolar lavage fluid.

In this procedure, rabbit anti-tryptase serum was coated onto a plate, the plate washed, and unbound sites blocked with bovine serum albumin, followed by another washing. The test fluid then was added to the plate and the plate incubated. The plates were washed and the mouse AA5 mAbs added to the plate. After another washing, biotinylated rabbit anti-mouse IgG was added, the plates washed again, and avidin-biotin-peroxidase complexes added to the plate. The plate was washed a final time, and developed by addition of p-nitrophenyl substrate (measurement taken at 490 nm). In this procedure, the powerful binding interaction between avidin and biotin is used to increase the binding efficiency between the rabbit anti-mouse IgG and the peroxidase conjugate.

Schwartz et al. (1994) describe ELISA's using murine monoclonal antibodies, specifically a murine mAb designated B12. As in the ELISA's described above, the B12 mAb was bound to a plate, washed and blocked, and tryptase added to the plate. Another murine monoclonal antibody was used as the detect antibody. This ELISA is described as having a detection limit of approximately 1 ng/ml. This reference notes that the monoclonal B12 antibodies appear to bind to a specific tryptase conformational epitope which is present in both the active tetramer form of tryptase and in deactivated tryptase in solution.

SUMMARY OF THE INVENTION

In view of the above discussion, it is a principal aim of the present invention to provide an immunoassay for human tryptase which is extremely sensitive, accurate, and precise, and which does not require the use of radioactive isotopes.

Another aim of the present invention is to provide a method whereby anti-human tryptase polyclonal antibodies having relatively low affinity for human tryptase are separated from anti-human tryptase polyclonal antibodies having relatively high affinity for human tryptase.

A further aim of the present invention is to provide a method for the generation of high affinity, anti-human tryptase polyclonal antibodies.

A still further aim of the present invention is to provide high affinity, anti-human tryptase polyclonal antibodies which are capable of the efficient capture of human tryptase from solution.

Yet another aim of the present invention is to provide enzyme-linked immunosorbent assays (ELISA) for human tryptase, and, more specifically still, a double antibody-sandwich ELISA for human tryptase which utilizes high affinity, anti-human tryptase polyclonal antibodies derived from arian species as the capture antibody, and murine-derived monoclonal antibodies as the detect antibody.

These and other objects, aims, and advantages of the present invention will become clear upon a complete reading of the Detailed Description and attached claims, below.

In summary, the present invention includes avian-derived anti-human tryptase polyclonal antibodies capable of capturing tryptase from solution.

The present invention also includes avian-derived anti-human tryptase polyclonal antibodies capable of capturing tryptase from solution which are produced by passing a heterogenous avian-derived IgY protein fraction over a human tryptase-bound affinity matrix, followed by elution of the non-tryptase-specific immunoglobulins from the matrix. Subsequent to elution of the non-specific immunoglobulins, a first fraction of anti-human tryptase polyclonal antibodies is eluted by washing the matrix with an aqueous buffered $MgCl_2$ solution to yield a first eluate, then a second fraction of anti-human tryptase polyclonal antibodies is eluted by washing the matrix with an aqueous buffered glycine solution to yield a second eluate. The second eluate contains the anti-human tryptase polyclonal antibodies capable of capturing tryptase from solution.

The present invention further relates to a double antibody-sandwich enzyme-linked immunosorbent assay for the detection of human tryptase. The ELISA of the present invention comprises capture antibodies and detection antibodies. The capture antibodies are avian-derived polyclonal tryptase-specific antibodies capable of capturing human tryptase from solution and the detection antibodies are monoclonal antibodies.

Additionally, the present invention relates to an immunoassay method for the detection of human tryptase which comprises contacting a sample to be tested for the presence of human tryptase with avian-derived polyclonal antibodies specific to human tryptase and capable of capturing human tryptase from solution, thereby forming an immune complex, followed by determining the presence of the immune complex. The presence of the immune complex serves as a measure of human tryptase in the sample.

The present invention also includes a method for isolating the high affinity tryptase-specific polyclonal antibodies used above. The method comprises inoculating an avian with tryptase and isolating immunoglobulins from serum taken from the avian or from the yolk of eggs laid by the avian. The immunoglobulins then are contacted to a tryptase-immobilized affinity matrix, thereby binding tryptase-specific immunoglobulins to the affinity matrix. Non-tryptase-specific immunoglobulins are then eluted from the affinity matrix. A first traction of low affinity tryptase-specific antibodies then are eluted from the affinity matrix by washing with a first buffered solution. A second fraction of high affinity tryptase-specific antibodies then are eluted from the affinity matrix by washing with a second buffered solution. The second traction of high affinity tryptase-specific antibodies then is collected for use in the ELISA's and methods described herein.

The present invention has many advantages over prior art methods for assaying tryptase. Foremost among these advantages is that the present assay does not require the use of radioactive reagents, which are inherently dangerous.

Another advantage of the presently described assay is that it is highly sensitive, being at least one order of magnitude more sensitive than prior art assays. The present assay method also is accurate, precise, and easy to assemble and use.

A further advantage of the present invention is that it utilizes polyclonal antibodies which are capable of capturing tryptase from solution. These polyclonal antibodies recognize many epitopes on the tryptase tetramer as well as on the individual tryptase subunits. In other words, the polyclonal antibodies of the present invention are capable of capturing both active and inactive forms of tryptase. This results in a synergistic increase in tryptase binding by the polyclonal antibody population as a whole. Additionally, the polyclonal antibodies do not hinder the enzymatic activity of tryptase.

DETAILED DESCRIPTION OF THE INVENTION

As noted above, a principle aim of the present invention is to provide highly sensitive, accurate, and precise immunoassays for human tryptase.

More specifically, the present invention relates to ELISA's which are capable of rapidly detecting and quantifying the amount of human tryptase in a sample, the high affinity polyclonal antibodies used in the ELISA's, and methods of generating the high affinity polyclonal antibodies.

Overview

The present invention includes a method for generating high affinity, anti-human tryptase polyclonal antibodies. These high affinity polyclonal antibodies then are used in immunoassays for human tryptase. The general protocol for isolating the high affinity, anti-human tryptase polyclonal antibodies used in the subject ELISA's precedes as follows:

First, avian species (e.g. chickens, turkeys, and the like) are immunized with multiple injections of native human tryptase to initiate an immunogenic response in the avians. After a suitable amount of time has elapsed to establish a high titer of anti-tryptase antibodies within the avians, serum or eggs are collected from the human tryptase-immunized arians.

The serum and egg yolks from the immunized birds contain a wide variety of antibodies specific for any number of antigens from natural exposure. The next step of the present process is to isolate the IgY fraction of immunoglobulins (which fraction is known to contain tryptase-specific antibodies) from the serum or egg yolks. This can be accomplished with the egg yolks by utilizing a commercial product, for instance, Promega Corporation's EGGstract™ IgY Purification System (Promega Corporation, Madison, Wis. U.S.A.). There also are a number of other methods for isolating immunoglobulins from egg yolks, such as other sequential precipitation methods, which are well known to those skilled in the art. (See, for instance, *Scopes* (1994), which is incorporated herein by reference for its teaching of protein purification methods). The conventional method of protein isolation, which is completely satisfactory to practice the present invention, is to "salt out" the protein fractions by precipitation of the proteins from a salt solution. The IgY polyclonal antibodies from the serum of the avians can be isolated using, for instance, chromatographical methods. Again, there are a number of methods well known to those skilled in the art for isolating immunoglobulins from serum or egg yolk samples.

The next step of the process is to separate the tryptase-specific polyclonal antibodies (pAbs) from the non-specific antibodies within the IgY fraction. To accomplish this, the isolated IgY fraction, which contains approximately two to ten percent tryptase-specific pAb is applied to an affinity column constructed by coupling human tryptase to a resin to create an affinity matrix. This enzyme-bound matrix will capture only those antibodies within the IgY fraction which are specific for human tryptase. The non-specific polyclonal antibodies within the IgY fraction are removed from the column by multiple washings with a simple saline buffer solution. This leaves the matrix containing only those polyclonal antibodies which are specific for human tryptase.

Once the non-specific polyclonal antibodies have been washed from the enzyme-bound matrix, the next step of the present process is to separate those pAbs which have relatively low affinity for tryptase from those pAbs which have a much higher relative affinity for human tryptase. This is accomplished by sequential elution of the column to yield two pools of specific pAbs: a first pool containing low affinity, anti-human tryptase pAbs, and a second pool containing high affinity anti-human tryptase pAbs.

The tryptase-specific polyclonal antibodies having low affinity are eluted from the matrix by washing the matrix with a "soft eluant," preferably about a 1M to about a 3M solution of $MgCl_2$. (This process will be referred to hereinbelow as "soft elution"). This will wash the low affinity pAbs from the matrix, while those pAbs having higher affinity for tryptase will remain firmly attached to the matrix. The eluate is collected in a first pool of low affinity anti-human tryptase pAbs. While these pAbs are inefficient at capturing tryptase from solution (which has a bearing on the sensitivity of ELISA's utilizing these pAbs), they find use in affinity purification resins and other useful applications.

The next step in the isolation of high affinity, anti-tryptase pAbs is to release the pAbs remaining on the matrix. Here, the high affinity, tryptase-specific polyclonal antibodies which remain fixed to the enzyme-bound matrix are removed from the affinity matrix by elution with a "hard eluant," such as a 0.01M to 0.1M glycine buffer, or a buffered aqueous acidic solution of $pH \leq 3$. (This process will be referred to hereinbelow as "hard elution"). The eluate is collected in a second pool of high affinity anti-human pAbs.

The high affinity tryptase-specific polyclonal antibodies so isolated are capable of capturing human tryptase from solution. The antibodies are highly specific for tryptase. Because they are polyclonal in nature, the antibodies recognize a variety of epitopes on tryptase. Coupled with the high specificity for tryptase of the antibodies, their binding to various epitopes increases the overall tryptase binding capacity of the pool of high affinity antibodies. The polyclonal antibodies isolated by the present process are capable of capturing both active and deactivated forms of tryptase from solution. Additionally, the polyclonal antibodies isolated by the present process will capture both the α and β isoforms of tryptase from solution.

The qualities of the polyclonal antibodies isolated by the present process make them particularly well suited for use in immunoassays, especially ELISA's. The polyclonal antibodies of the present invention are preferably used as capture antibodies in a double antibody-sandwich ELISA, with monoclonal or polyclonal anti-tryptase antibody acting as the detect antibody. Each of the above steps will now be described in greater detail.

Preparation of Human Tryptase

Human tryptase to initiate the immune response in the avians to generate the polyclonal antibodies of the present invention can be prepared from human lung tissue as follows: The tissue is first blended with an equal volume of distilled water and centrifuged at 20,000×g for 20 minutes at 5° C. The precipitated bead then is re-suspended in a low salt buffer (e.g. 0.15M NaCl, 20 mM morpholinethane sulfonic acid (MES) and 0.02% sodium azide, pH 6.1), blended, and again centrifuged as before. This process is repeated five times. The bead is then re-suspended in a high salt buffer (2M NaCl, 10 mM MES, and 0.02% sodium azide, pH 6.1) and centrifuged at 20,000×g at 5° C. for 20 minutes. This process is repeated at least three times and the supernatant from each extraction retained and pooled. Material contained in the pooled supernatant is then precipitated by the addition of ammonium sulphate to 2M, and the supernatant retained.

The supernatant from ammonium sulphate precipitation is loaded onto an octyl-Sepharose (Pharmacia) column equilibrated with 10 mM MES, 2M ammonium sulphate, and 0.02% sodium azide, and washed with the same solution. A tryptase-rich fraction is then eluted from the column by washing with a solution of 0.7M NaCl, 0.7 M ammonium sulphate and 0.02% sodium azide. The elution of the column can be monitored by measuring absorbance at 280 nm, or by measuring tryptic activity with synthetic substrates such as benzoyl DL-arginine p-nitroanilide (BAPNA, Aldrich Chemical Co.. Milwaukee, Wis., U.S.A.), or tosyl L-arginine methyl ester (TAME, Aldrich). Human lung tryptase also can be purchased commercially from ICN Pharmaceuticals and Athens Research Tech, among others.

Immunization of Avians and Isolation of IgY Fraction

Polyclonal antibodies to human tryptase are produced by eliciting an immunogenic response in chickens, turkeys, or other avian species by injection with human tryptase. In the preferred protocol, the avians, preferably chickens or turkeys, are inoculated with an initial injection of tryptase (preferably in the form of an emulsion in complete Freund's adjuvant or similar adjuvant), followed by three booster injections of tryptase (preferably in the form of emulsions in incomplete Freund's or similar adjuvant). This protocol initiates an immunogenic response in avians resulting in high tilers of tryptase-specific antibodies in the birds.

Serum and/or eggs are then harvested from the avians so inoculated.

The IgY fraction of immunoglobulins then is isolated from the egg yolks or serum from the inoculated avians. As noted above, this can be accomplished by sequential precipitation, preferably using a commercially available reagent kit such as the EGGstract™ system (Promega Corporation). Other conventional methods of protein isolation, such as chromatographic methodologies (i.e., gel filtration, ion-exchange, or affinity chromatography) can be used to accomplish this same result with equal success. For a complete discussion of protein purification, see, for instance, R. G. Harrison, "Protein Purification for Process Engineering" or R. K. Scopes, "Protein Purification, Principles and Practice," both of which are incorporated herein by reference for their teaching of protein purification methods.

Avian species were chosen because they are phylogenetically more distant from humans than are other commonly used animals for the production of pAbs, such as rabbits, goats, and guinea pigs. While not being confined to any particular causative mechanism or mode of operation, it is believed that the greater phylogenetic distance between humans and avians as compared to humans and other mammals evokes a higher immunogenic response to human tryptase in the avians used to produce the polyclonal antibodies. The polyclonal antibodies produced by the avian response appear to have increased affinity and specificity to human tryptase than antibodies produced by commonly used mammalian species.

Figure 3:
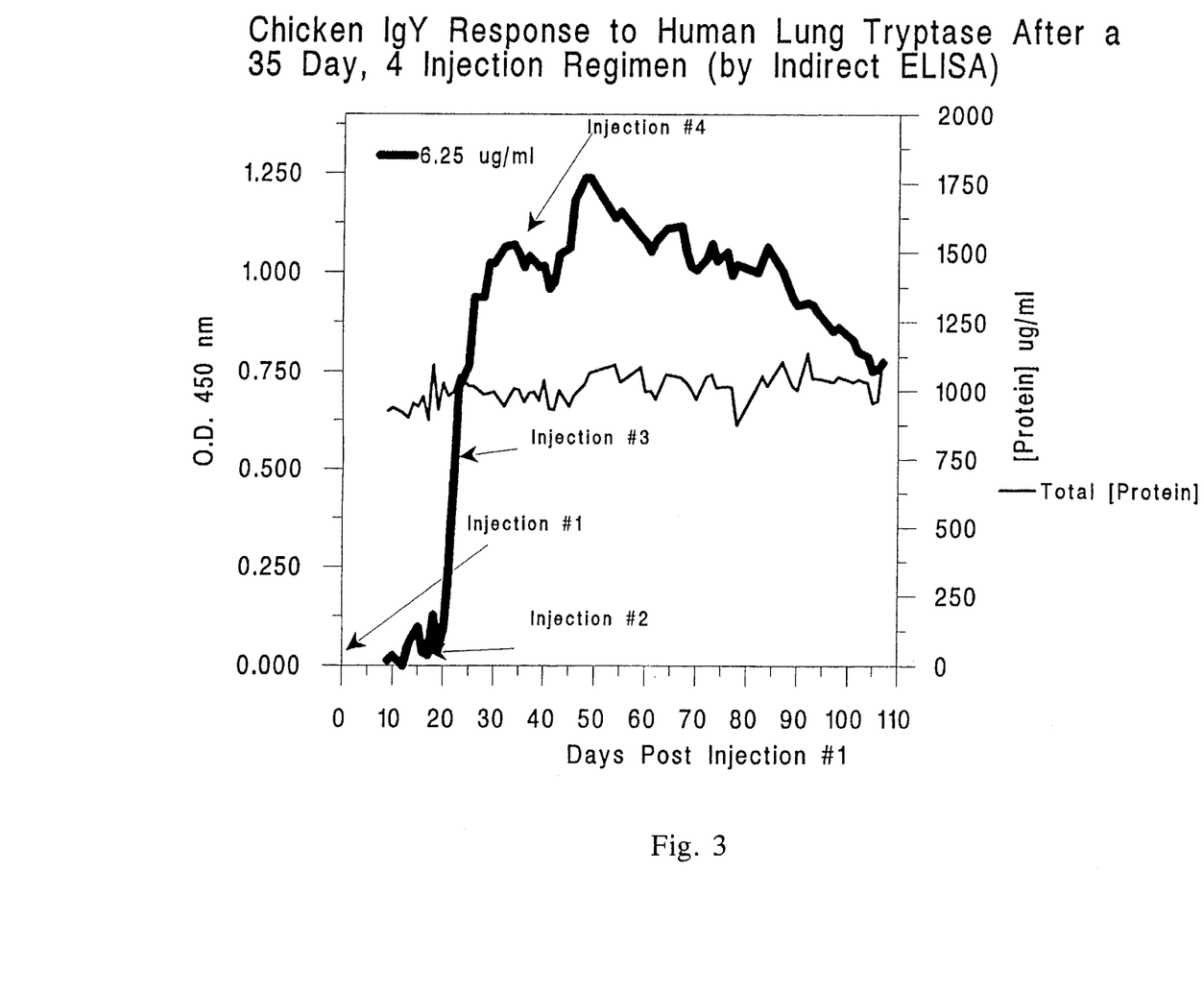
FIG. 3 is a graph showing the IgY response levels over time in chickens after a 35 day, 4-injection inoculation protocol with human lung tryptase.

An exemplary inoculation scheme is depicted graphically in FIG. 3. Here, a specific-pathogen-free (SPF) Leghorn chicken between 12 to 16 weeks of age and functionally laying was immunized over a 35 day period with 4 injections of human lung tryptase. The first injection contained 50 μg human lung tryptase emulsified in complete Freund's adjuvant. Three additional injections of 50 μg human lung tryptase emulsified in incomplete Freund's adjuvant were administered at Days 15, 21, and 35 post-vaccination. Egg collection began 8 days after the first injection.

Figure 4:
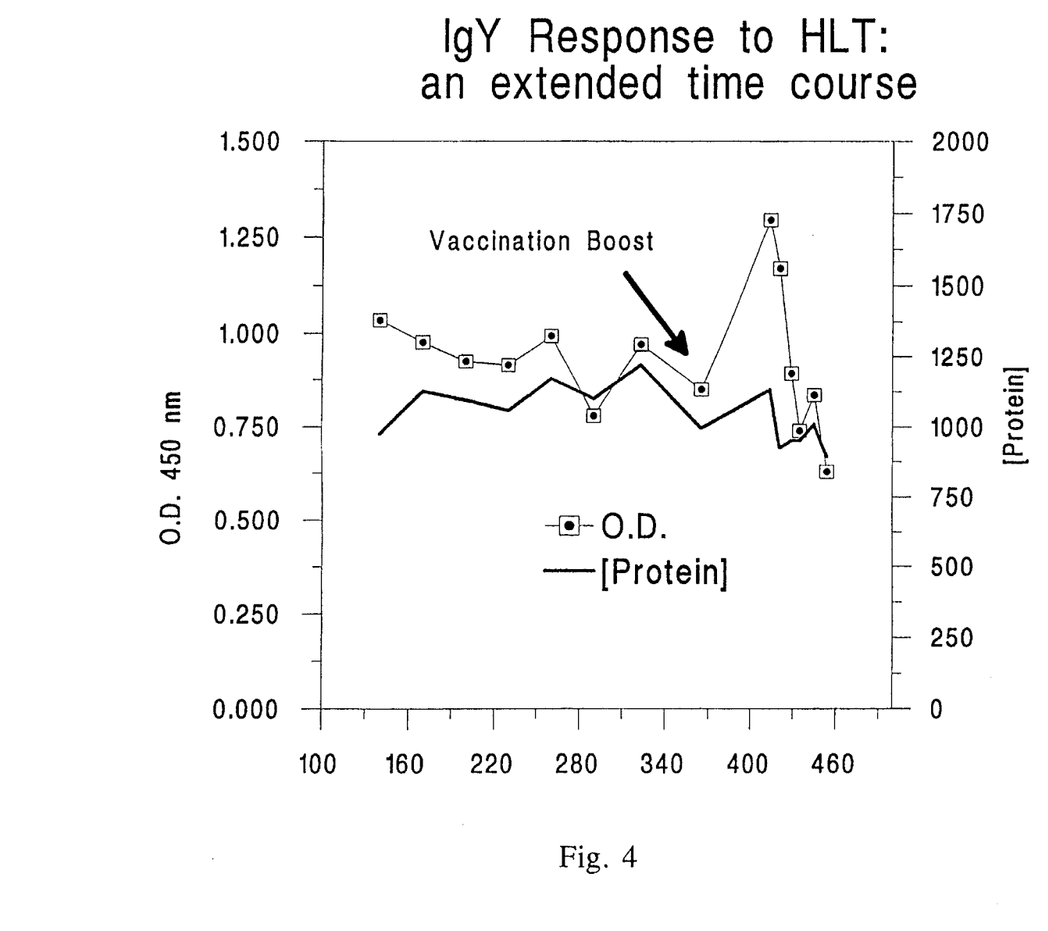
FIG. 4 is a graph showing the extended time course IgY response in chickens after inoculation with human lung tryptase as in FIG. 3.

FIGS. 3 and 4 show the response of the chicken to the above-described inoculation protocol. FIG. 3 plots the total protein (thin line) and IgY fraction (bold line) over time from Day 1 through Day 110. FIG. 4 shows a long-range plot of the IgY response over time from Day 100 to Day 460. A vaccination boost shows that a significant amnestic response to tryptase was observed.

It should be noted that at present it remains unclear whether adjuvant is required to ellicit an adequate immunological response, or whether other adjuvants such as TITERMAX adjuvant, RIBI adjuvant, or alum will function with equal success. Booster timing is probably not critical, but should preferably fall as near to 14, 21, and 28 days post-primary vaccination as possible. Antigen dosage in the above exemplary vaccination schedule was chosen to be limiting, thereby driving clonal selection toward high affinity maturation in order to yield a polyclonal population of antibodies with increased affinity for tryptase.

Tryptase Affinity Column and Isolation of Polyclonal Antibodies

Once the IgY fraction of immunoglobulins has been isolated, the non-specific antibodies are separated from the tryptase-specific antibodies. This is accomplished most efficiently by the use of an enzyme-bound affinity column.

A tryptase-specific affinity column is utilized to isolate the polyclonal anti-tryptase antibodies from the proteins extracted from the egg yolks. A suitable tryptase-specific affinity matrix can be constructed by coupling native human tryptase to p-nitrophenol chloroformate-activated agarose. As noted by many of the references cited above, human tryptase can be isolated from a wide variety of tissues. Preferably, the present invention utilizes tryptase isolated from human lung tissue. However, tryptase isolated from any type of MC will suffice.

The preferred method of constructing the affinity column is to couple purified human lung tryptase to a p-nitrophenol chloroformate-activated agarose resin (Sigma) in a manner consistent with the method of Livingston et al. (1975), which is incorporated herein in its entirety for its teaching of preparing affinity matrices.

Specifically and preferably, tryptase is concentrated and dialyzed to 2 mg/ml, and applied to the support resin in a coupling buffer containing 100 mM $NaHCO_3$ and 500 mM NaCl at pH 8.0

The tryptase-coupled affinity matrix then is gently loaded into a conventional chromatographic column or other suitable vessel. The IgY fraction of the egg yolks or serum from the immunized chickens is placed at the head of the tryptase affinity column and the column eluted using suitable buffers.

An initial washing of the affinity matrix with standard buffer solutions (such as phosphate-buffered saline (PBS) or tris-buffered saline (TBS)) removes those antibodies which are not specific for tryptase, while the tryptase-specific antibodies remain fixed to the matrix. The initial eluate can be discarded because the antibodies contained therein are not specific for tryptase.

The tryptase-specific antibodies which remain bound to the affinity column are then eluted in two successive fractions. A first fraction of "soft eluate" antibodies are those antibodies which are removed from the affinity matrix under relatively mild elution conditions. The preferred eluant in this case is an aqueous, buffered solution of from 1M to 3M $MgCl_2$.

There is at this time no known salt equivalent of $MgCl_2$ at a variety of concentrations and pH's for the removal of the first pool of anti-tryptase pAbs. Continuing experimentation suggests that this "soft elution" phenomena is unique to $MgCl_2$. The phenomenon is pH independent from pH 4 to pH 9.

Figure 5:
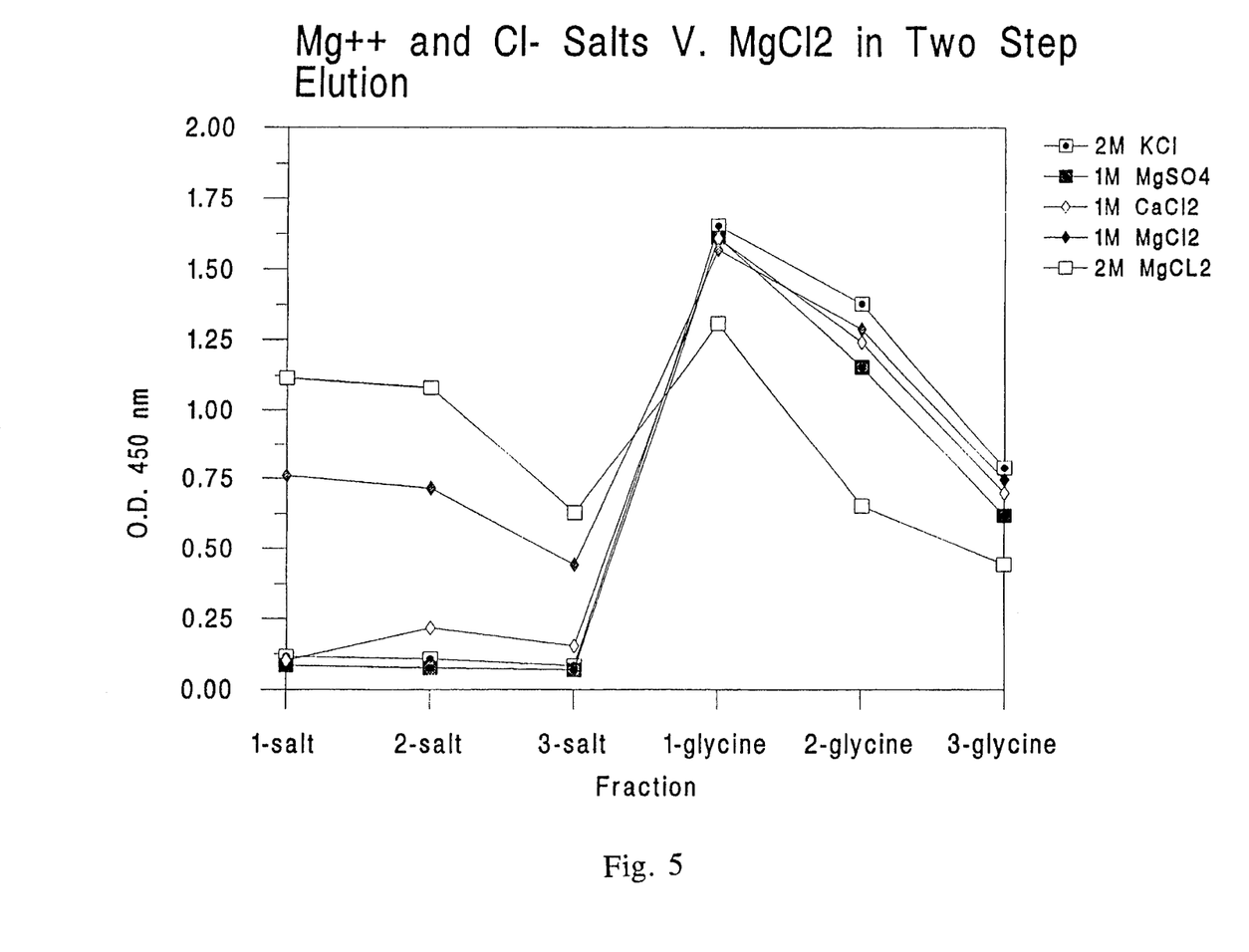
FIG. 5 is a graph showing the efficacy of various sodium and chloride salts as compared to magnesium chloride in a two-step elution of polyclonal chicken anti-human lung tryptase antibodies from a tryptase affinity column.

A comparison of the elution profiles of other magnesium and chloride salts is shown in FIG. 5. Here, an affinity column was loaded with the IgY fraction from egg yolks, and washed with three volumes of a first salt (designated 1-salt, 2-salt, 3-salt on the x axis), and then washed with three volumes of glycine (1-glycine, 2-glycine, 3-glycine). As FIG. 5 clearly shows, both 1M and 2M $MgCl_2$ resulted in a relatively large first pool of pAbs being washed from the column. The amount of pAbs eluting in the first pool is decreasing significantly by the third washing. (Further washings with $MgCl_2$, not shown, indicate that the amount of pAbs removed from the column decreases to the baseline.) Subsequent treatment with glycine resulted in an even larger second pool of pAbs eluting from the column. This elution profile was not exhibited by the other magnesium and chloride salts tested (2M KCl, 1M $MgSO_4$, and 1M $CaCl_2$).

Figure 6:
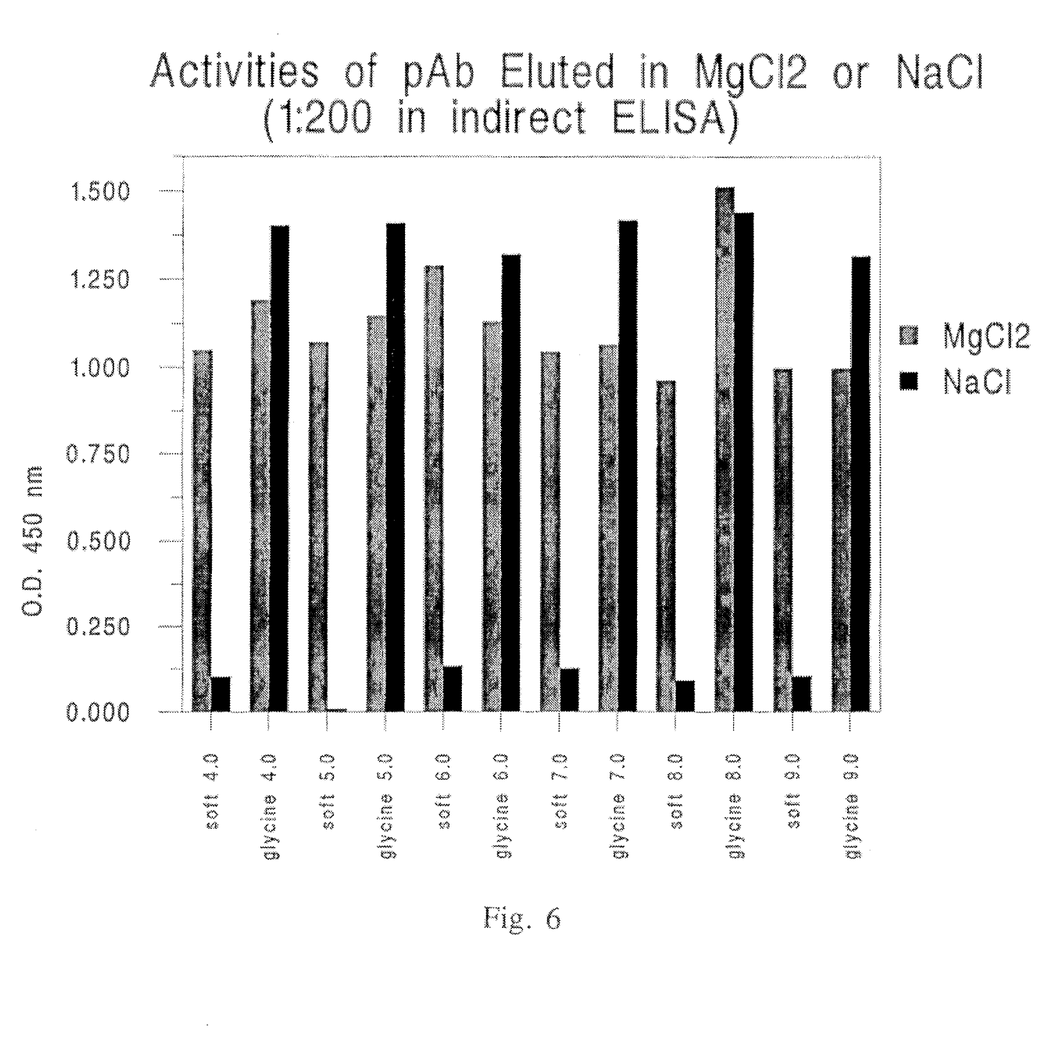
FIG. 6 is a bar graph comparing the activities of polyclonal anti-human lung tryptase antibodies eluted from a tryptase affinity column using either NaCl or $MgCl_2$ of varying pH.

FIG. 6 depicts the activity of the pAbs eluted from the affinity column using either $MgCl_2$ or NaCl as the "soft eluant" at various pH's. In each run, glycine was used as the second, or "hard eluant." Each pair of columns marked "soft" (one for $MgCl_2$, the other for NaCl) measures the activity of the pAb pool eluted from the column with the "soft" eluant. The next pair of columns, marked "glycine," measures the activity of the pAbs subsequently eluted from the column by washing with glycine. As can be seen, $MgCl_2$ results in both a consistently large first elution pool, and a consistently large second elution pool. In contrast, NaCl displays a distinctly different elution profile: very little antibody is removed from the column using NaCl, leaving most of the antibody to be removed in a single pool by washing with glycine.

FIG. 6 also graphically shows the relative insensitivity of the $MgCl_2$ eluant to pH effects.

Urea, a chaotrope, does demonstrate "soft elution" properties at high concentrations (8M). However, urea is well known and infamous for destroying the activity of antibodies and antigens.

Figure 7:
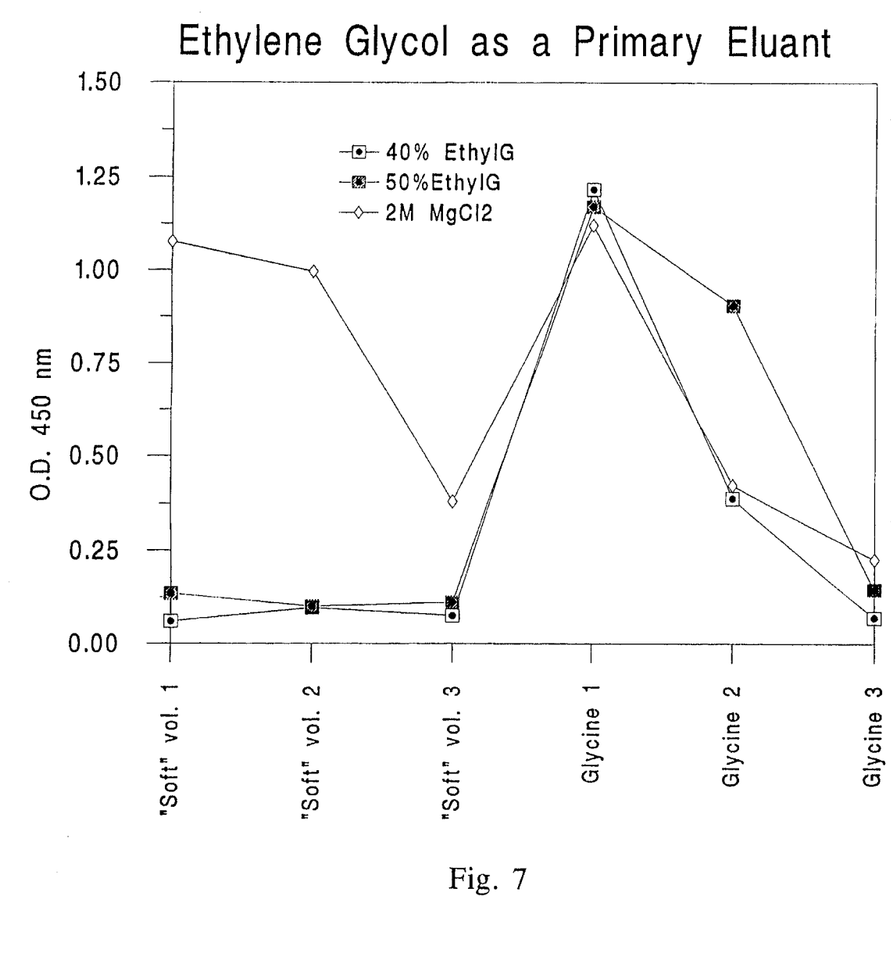
FIG. 7 is a graph depicting the efficacy of ethylene glycol as a primary eluant as compared to $MgCl_2$ in a two-step elution of polyclonal chicken anti-human lung tryptase antibodies from a tryptase affinity column.

FIG. 7 depicts an attempt at using ethylene glycol as a primary or "soft" eluant. However, as depicted in FIG. 7, solutions of 40% and 50% ethylene glycol do not elute a significantly large volume of pAbs as compared to $MgCl_2$.

The first pool of antibodies which elute from the affinity matrix under these conditions (1M to 3M $MgCl_2$) has a relatively low affinity for tryptase, and is collected in a first pool. These antibodies are the soft elute antibodies. While specific for tryptase, the soft elute pool of pAbs generally does not have sufficient binding ability to efficiently capture tryptase from solution.

The tryptase-specific antibodies which remain affixed to the affinity matrix are then eluted in a second fraction of "hard eluate" antibodies. These antibodies are removed from the affinity matrix under more rigorous conditions. The preferred eluant for the second fraction of antibodies is a buffered aqueous solution of from about 0.01M to about 0.1M glycine. This eluate is collected in a second pool of antibodies which has high affinity for tryptase. These pAbs have the ability to efficiently capture human tryptase from solution. Other "hard elution" buffers can be used in place of glycine. These include low pH ($\leq 3$) aqueous buffers (such as citrate buffers) and dilute sodium hydroxide solutions.

It has been found that multiple purifications of IgY proteins as described above can be performed using the tryptase-coupled activated agarose matrix with no visible loss of separation efficiency.

The successive elution protocol of the present invention effectively enriches the second elution pool for only those antibodies having the greatest affinity for tryptase. It is this second pool of high affinity, anti-tryptase pAbs which is used as a capture reagent in the immunoassays described herein. This second pool of antibodies is capable of detecting both enzymatically active and enzymatically inactive tryptase, as well as both the α and β forms of human tryptase. Moreover, the second pool of polyclonal antibodies is incapable of neutralizing the enzymatic activity of tryptase. Therefore, the epitopes to which the pAbs interact are presumably sufficiently distant from the active site of the tryptase so as not to adversely affect its protease activity.

Immunoassays for the Detection and Quantification of Tryptase

The high affinity and specificity of the hard elute pAbs for tryptase as described above make them ideal for use in immunoassays for the detection and quantification of tryptase levels in solution. Of particular merit is the fact that the anti-tryptase pAbs described herein can be incorporated into an immunoassay which is capable of detecting tryptase levels as low as 20 pg/ml. This level of sensitivity is at least 100 times greater than the sensitivity of Pharmacia's commercially-available RIACT RIA system described above, and more than 10 times greater than the sensitivity of the immunoassay described by Schwartz et al. (1994).

As noted in the Description of the Prior Art, ELISA's are a widely known and employed type of immunoassay. Their widespread acceptance in the research and clinical community stems in large part from their extended linear response range and the fact that ELISA's do not utilize radioactive reagents. ELISA's can be fashioned in a number of different configurations, including indirect ELISA's, direct competitive ELISA's, antibody-sandwich ELISA's, and double antibody-sandwich ELISA's. Each of these different configurations utilize the same basic interactions between enzymes, antigens, and enzyme/antibody conjugates. All of these various types of ELISA's are well known to those of skill in the art. For instance, for a complete description of ELISA construction techniques see *Current Protocols in Molecular Biology* (1994): Vol. 2, Chapter 11, Wiley Press, incorporated herein by reference for its teaching of ELISA protocols.

The high affinity, anti-human tryptase polyclonal antibodies of the present invention are capable of acting as capture or detect antibodies in all of the types of ELISA's described above. For sake of clarity and brevity only, the remainder of the Detailed Description shall be limited to a discussion of the most complicated type of ELISA, a double antibody-sandwich ELISA. It is understood, however, that the anti-tryptase polyclonal antibodies of the present invention will function with equal success in any ELISA, regardless of construction. It is further understood that the construction of such various ELISA's is well known to one of skill in the art.

Figure 1:
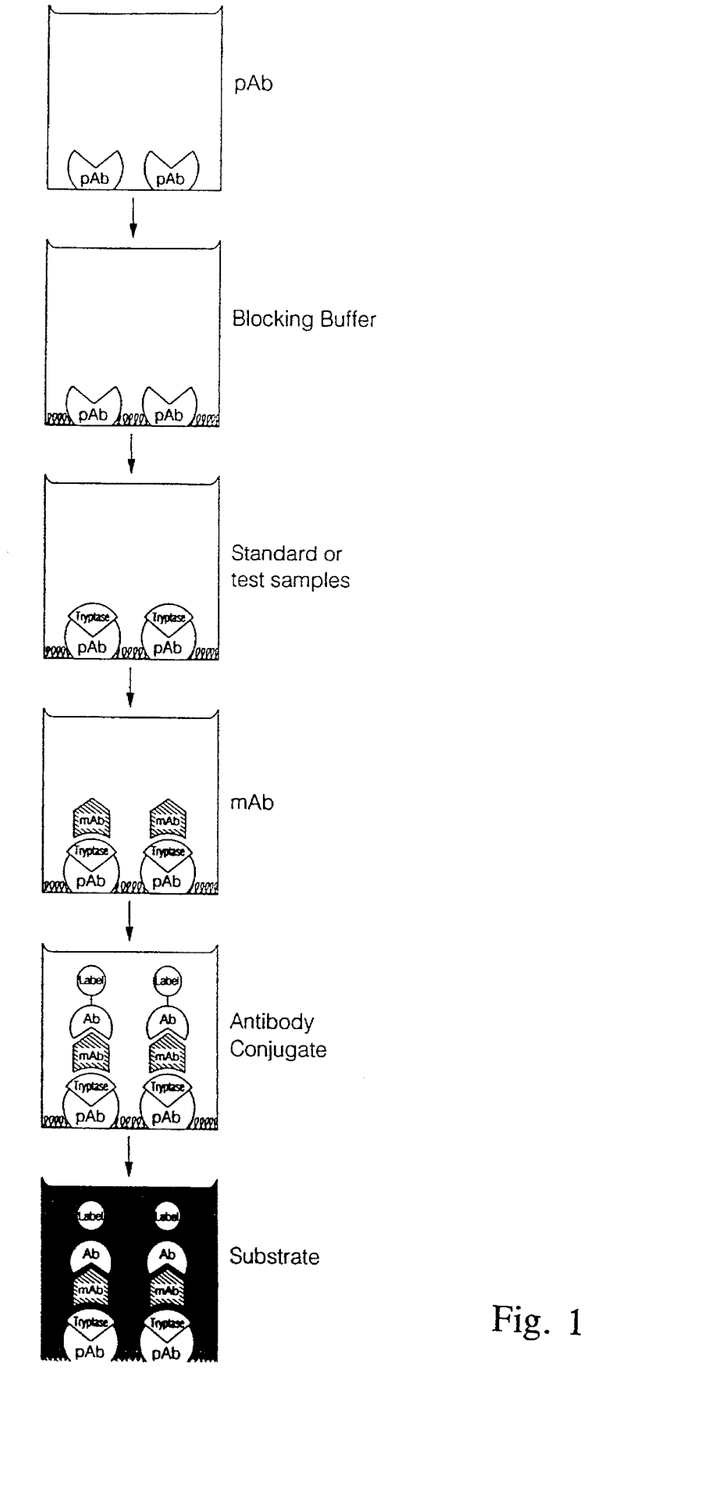
FIG. 1 is a schematic representation of a double antibody-sandwich enzyme-linked immunosorbent assay for the detection of human tryptase according to the present invention.

Double antibody-sandwich ELISA's are an especially useful methodology when screening for specific antibodies in cases where a small amount of specific antibody is available and purified antigen is unavailable. Additionally, this ELISA method is often used for epitope mapping of different monoclonal antibodies that are directed against the same antigen. Construction of a double antibody-sandwich ELISA according to the present invention is illustrated in FIG. 1, and proceeds as follows:

First, suitable microtiter plates are coated with capture antibodies specific for the immunoglobulin. In the present invention, the capture antibodies are taken from the second pool of hard eluant polyclonal antibodies derived from immunized avians, preferably chickens. In FIG. 1, the capture antibody is designated pAb. This is done by coating the microtiter plates with a solution of pAb and incubating for 8 to 48 hours at 4° C. The coated plates are then thoroughly rinsed with a solution of tris-buffered saline with TWEEN™ 20 (TBST). Non-specific residual binding to the microtiter plate itself is then blocked by coating the plate with a blocking buffer. A commonly used blocking buffer is a solution of 0.05% TWEEN™ 20 containing bovine serum albumin (BSA). The plates are again rinsed with TBST.

The solutions to be tested are then diluted in the blocking buffer. Preparing a number of serial dilutions is recommended. The plates are then coated with the test solutions and incubated for at least two hours at room temperature.

After incubation the plates are again rinsed with TBST. Other buffered solutions, such as phosphate-buffered saline or phosphate-buffered saline with TWEEN™, also may be used.

At this point in the process, the plate appears schematically as shown in the third drawing from the top in FIG. 1. The tryptase being assayed has been captured by the polyclonal antibodies which are fixed to the bottom of the microtiter plate.

The next step is to introduce a tryptase detect antibody solution which will bind to the captured tryptase. Either polyclonal anti-tryptase antibody or monclonal anti-tryptase antibody can be used as the detect antibody. The preferred detect antibody is a murine-derived monoclonal antibody specific to tryptase. More preferred still is that the detect antibody be the murine monoclonal antibody designated AA5, as described by Walls et al. (1990a and 1990b), both of which are incorporated herein by reference for their teaching of the production of the monoclonal antibody designated AA5. A solution of the monoclonal antibody is prepared and the wells are coated and incubated for at least two hours at room temperature. After incubation, the plates are again washed with TBST.

The preferred AA5 murine monoclonal detect antibody may be prepared by subcutaneously injecting mice with 0.25 mg tryptase in complete Freund's adjuvant at Day 0, followed by additional injections (0.25 mg, incomplete Freund's adjuvant) at Day 28 and Day 56. At Day 80, the mice are injected intravenously with 0.1 mg tryptase in saline. Three days later, lymphocytes from two separate spleens are fused with NS-1 (P3-N3-1/1-Ag 4.1) mouse myeloma line at a ratio of 2:1 using standard and well-known methodologies. Hybridomas cells secreting IgG specific for tryptase are then identified by any known means for tryptase identification. AA5 was subcloned by limiting dilution, followed by generation of ascites fluid in pristane-primed mice to yield the AA5 mAB.

The plates are rinsed with TBST, and are then coated with a conjugate specific antibody/horseradish peroxidase conjugate. Such antibody/horseradish peroxidase conjugates are well known in the art. A conventional method to prepare such conjugates includes using sodium periodate to oxidize the carbohydrate side chains of horse radish peroxidase, followed by the formation of a Schiff base between the activated peroxidase and amino groups of the antibody. The preferred antibody for the conjugate is goat anti-mouse IgG antibodies. The Schiff base then is reduced (sodium borohydride) to yield a stable antibody/enzyme conjugate. The wells of the microtiter plates then are incubated for at least two hours at room temperature. It is important here that the conjugate antibodies must not react with the capture antibody or the tryptase itself.

Here, it is preferred that the plates be rinsed with TBS three times prior to addition of the substrate.

A horseradish peroxidase substrate solution is then added to each well and the wells incubated for one hour at room temperature. The wells then are examined spectrophotometrically at 450 nm. For colorimetric detection, horseradish peroxidase-conjugated anti-mouse antibody used in conjunction with the substrate 3,3',5,5'-tetramethylbenzidine (TMB) is preferred. Other peroxidase substrates, such as o-phenylenediamine dihydrochloride (OPD) and anti-mouse alkaline phosphatase conjugates function with equal success.

The colorimetric double antibody-sandwich ELISA according to the present invention as described above has a sensitivity of about 20 pg/ml, a linear response range from 15 to 2000 pg/ml, and an r≧0.99.

A distinct advantage of the presently described ELISA is that the capture antibodies are high affinity polyclonal antibodies, as opposed to conventionally-used monoclonal antibodies or polyclonal antibodies. This is advantageous because it yields a synergistic increase in the binding efficiency of the capture layer. The synergistic effect results from the heterogenous nature of the epitopes in this population of polyclonal antibodies. A comparison between polyclonal and monoclonal antibodies will help illustrate this point:

A population of monoclonal antibodies is homogenous. All of the monoclonal antibodies recognize the same epitope on the target molecule, and all of the monoclonal antibodies have the same affinity. For binding purposes, all of the molecules of a monoclonal antibody population are identical in both form and function. In contrast, the present ELISA is constructed using polyclonal antibodies, which are heterogeneous. While all of the polyclonal antibodies are highly specific for tryptase, they are not derived from a single clone, and therefore have variations in structure and in their binding mechanism. The polyclonal antibodies have different binding affinities from each other and recognize different epitopes on the tryptase molecule.

This is advantageous because it results in a synergistic cooperative effect in binding. Because the heterogenous population of polyclonal antibodies binds to the tryptase target at different epitopes, with different affinities, the overall efficiency of target binding is synergistically increased (i.e., higher avidity). While the entire population of polyclonal antibodies is both specific for tryptase and has a high affinity for tryptase, that specificity and affinity is accomplished differently by the different types of antibodies present in the high affinity pool of polyclonals. The relatively large size of the tryptase target molecule also adds to this synergism by providing a large number of epitopes. This also helps explain why the polyclonal antibodies of the present invention are capable of capturing both active and inactive forms of tryptase.

Anti-Tryptase Monoclonal Antibodies

As noted above, the detect antibody used in the subject immunoassays, and the double antibody-sandwich ELISA described immediately above, is preferably a monoclonal anti-tryptase antibody. The antibody is preferably derived from mice. A large number of such anti-tryptase antibodies are known.

The preferred anti-tryptase antibody is produced from the human lung tryptase-specific hybridoma clone designated AA5. This clone was first produced and characterized by Dr. Andrew Walls and co-workers at the University of Southampton, the United Kingdom. (See Bibliography). This monoclonal antibody currently is purified from tissue culture supernate from the growing clone by passing the fluid over a protein G affinity column. This purification step not only concentrates the antibody, but also removes the fetal bovine serum used to supplement the growing hybridoma. This monoclonal antibody is the preferred detection antibody in the subject double antibody-sandwich ELISA. The AA5 monoclonal antibody is capable of recognizing both enzymatically inactive and enzymatically active forms of tryptase.

Goat Anti-Mouse Horseradish Peroxidase Conjugate Antibody

The antibody/enzyme conjugate used in the above-described double antibody-sandwich ELISA is available from the Promega Corporation. This conjugate is prepared in a 5–30 ug/ml chicken IgY pre-immune Tris buffered saline with TWEEN™ solution.

Buffers

The polyclonal antibodies are preferably coated to the microtiter plates using a 0.025M bicarbonate buffer, pH 9.7. Preferably, the polyclonal antibody is coated on the microtiter plates by overnight incubation at 4° C.

All other reagents are preferably diluted using TBS with 0.05% v/v TWEEN™ 20 (TBST). Other equivalent buffered solutions, such as phosphate-buffered saline or phosphate-buffered saline with TWEEN can be used with equal success.

Blocking of the microtiter plates is preferably achieved using a one percent w/v bovine serum albumin (fraction V) in TBST.

All washes are preferably conducted using TBST, except for the final three washes prior to substrate addition, which are preferably done using TBS.

EXAMPLES

The following examples are provided for illustrative purposes only. The examples are understood not to limit the invention described herein in any manner.

Example 1

Construction of Standard Curve for Tryptase Double Antibody-Sandwich ELISA

Figure 2:
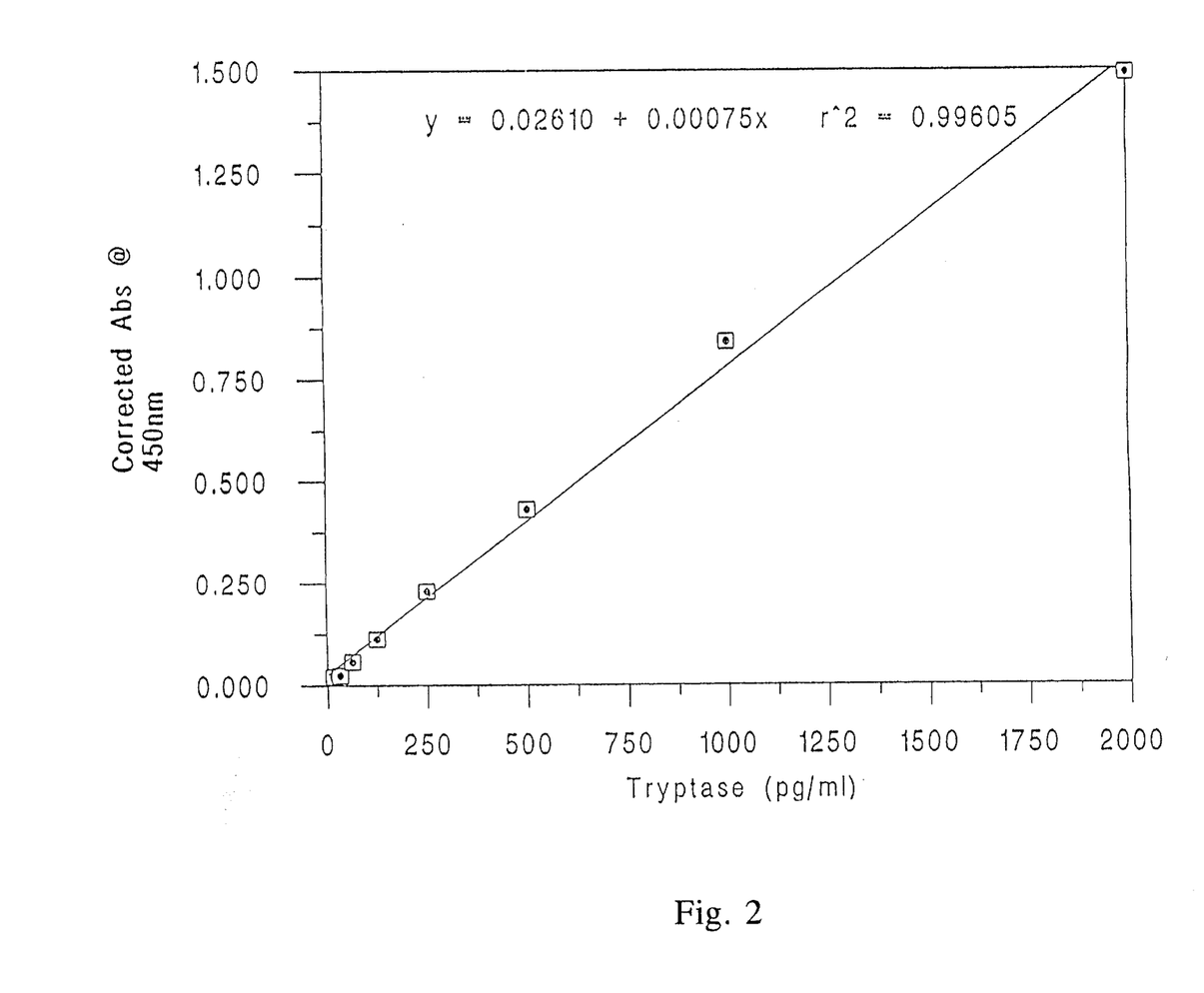
FIG. 2 is a standard curve for the human tryptase double antibody-sandwich ELISA shown schematically in FIG. 1.

A standard curve for the double antibody-sandwich ELISA for the detection of human tryptase described above is shown in FIG. 2. The curve was constructed using serially diluted tryptase solutions. The Y-axis represents corrected absorbance at 450 nm, while the X-axis represents tryptase concentration in picograms per milliliter of solution. Clearly, the present ELISA is far more sensitive than the prior art tryptase assays.

Example 2

Use of ELISA to Quantify Tryptase Release From Mast Cells

The double antibody-sandwich ELISA described above was used to analyze the release of tryptase from mast cells. In this example, the mast cell line HMC-1 was utilized. In short, HMC-1 cells were cultured in standard fashion. Mid-log growth phase HMC-1 cells were then washed and re-suspended in serum-free culture media. The mitogens phorbol myristate acetate (PMA) and Concanavalin A (ConA), the secretagogues calcium ionophore (CaI) and Compound 48/80, the neuropeptide Substance P (SP), and growth promoter Stem Cell Factor (SCF) were then added to the cultures. Aliquots were removed at 0, 1, 2, and 4 hours. The samples were analyzed for cellular viability by both trypan blue exclusion and lactate dehydrogenase (LDH) release. Tryptase release was then measured using the double antibody-sandwich ELISA of the present invention.

Using this standard curve, it was found that PMA induced the greatest tryptase release, at about 1 hour post-inoculation. CaI, ConA and SCF appear to be initiators of late tryptase release, while SP and compound 48/80, which are known potentiators of histamine release, demonstrated no tryptase release above spontaneous levels.

It is understood that the present invention is not limited to the particular embodiment, reagents, steps, or methods described herein, but embraces all such forms thereof as come within the scope of the attached claims.

BIBLIOGRAPHY

Amon, U., et al, (1993), "Investigations on Plasma Levels of Mast Cell Mediators in Acute Atopic Dermatitis," *Journal of Dermatological Science* 7, 63–67.

Beyer, K., et al., (1994), "Serum Tryptase and Urinary 1-Methylhistamine as Parameters for Monitoring Oral Food Challenges in Children," *Int Arch Allergy Immunol.*, 104:348–351.

Hattori, T., et al., (1989), "Involvement of Tryptase-Related Cellular Protease(s) in Human Immunodeficiency Virus Type 1 Infection," Elsevier Science Publishers B. V. (Biomedical Division), 248:48–52, No.1,2.

Johnston, S. L., et al., (1993), "The Effect of Local Hyperthermia on Allergen-Induced Nasal Congestion and Mediator Release," *J. Allergy Clin. Immunol.*, 92:850–856.

Lavens, S. E., et al., (1993), "A Sensitive Colorimetric Assay for the Release of Tryptase from Human Lung Mast Cells In Vitro," *Journal of Immunological Methods*, 166:93–102.

Lavery, J. P. and Lisse, J. R., (1994), "Preliminary Study of the Tryptase Levels in the Synovial Fluid of Patients with Inflammatory Arthritis," *Annals of Allergy*, 72:425–427.

Little, S. S. and Johnson, D. A., (1995), "Human mast cell tryptase isoforms: separation and examination of substrate-specificity differences," *Biochem J.*, 307:341–346.

Livingston et al., (1975), *Methods in Enzymology*, 34:723–731.

Niles, A. L., et al., (1995), "Mast Cell Secretagogues in Bladder Inflammation," 9th International Congress of Immunology, Promega Corporation.

Nilsson. G. and Schwartz, L. B., (1994), "Mast-Cell Heterogeneity: Structure and Mediators," Blackwell Scientific Publications, Boston, pp. 195–208.

Ohtsuka, T., et al., (1993), "Time Course of Plasma Histamine and Tryptase Following Food Challenges in Children With Suspected Food Allergy," *Annals of Allergy*, 71:139–146, No. 2.

Pharmacia Tryptase RIACT RIA Article.

Platt, M. S., et at., (1994), "Involvement of Mast Cells in Sudden Infant Death Syndrome," *J. Allergy Clin. Immunol.*, 94:250–256.

Rasp, G. and Hochstrasser, K., (1993), "Tryptase in Nasal Fluid is a Useful Marker of Allergic Rhinitis," *Allergy*, 48:72–74.

Sant, G. R. and Theoharides, T., (1994), "The Role of the Mast Cell in Interstitial Cystiris," *Urologic Clinics of North Americ*, 31:41–53.

Schneider, E., et al., (1992), "Determination of Human Mast Cell Tryptase by Bioluminescence-Enhanced Two-Site Immunometric Assay," *Eur. J. Clin. Chem. Clin. Biochem.*, 30:871–873.

Schwartz, L. B., et al., T., (1987a), "Tryptase Levels as an Indicator of Mast-Cell Activation in Systemic Anaphylaxis and Mastocytosis," *The New England Journal of Medicine*, 316:1622–1626.

Schwartz, L. B., et al., (1987b), "Quantitation of Histamine, Tryptase, and Chymase in Dispersed Human T and TC Mast Cells," *The Journal of Immunology*, 138:2611–2615, No. 8.

Schwartz, L. B., et al., (1994), "Development of a New, More Sensitive Immunoassay for Human Tryptase: Use in Systemic Anaphylaxis," *Journal of Clinical Immunology*, 14:190–204.

Schwartz, L. B., (1995), "Structure and Function of Human Mast Cell Tryptase," *Biological and Molecular Aspects of Mast Cell and Basophil Differentiation and Function*, chapter 14:161–173, Raven Press, Ltd: New York.

Scopes, R. K., (1994), "Protein Purification, Principles and Practice," Springer-Verlag: New York.

Walls, A. F., et al., (1990a), "Production and Characterization of Monoclonal Antibodies Specific for Human Mast Cell Tryptase," *Clinical and Experimental Allergy*, 20:581–589.

Walls, A. F., et al., (1990b), "Immunohistochemical Identification of Mast Cells in Formaldehyde-Fixed Tissue Using Monoclonal Anitbodies Specific for Tryptase," *Journal of Pathology*, 162:119–126.

Walls, A. F., et al., (1991), "Mast Cell Tryptase and Histamine Concentrations in Bronchoalveolar Lavage Fluid from Patients with Interstitial Lung Disease," *Clinical Science*, 81:183–188.

Watkins, J., et al., (1993), "Improved Diagnosis of Anaphylactoid Reactions by Measurement of Serum Tryptase and Urinary Methylhistamine," *Ann Fr Anesth Rèanim.*, 12:169–172.

Wenzel, S., et al., (1986), "Immunoassay of Tryptase from Human Mast Cells," *Journal of Immunological Methods*, 86:139–142.

What is claimed is:

1. A method for isolating high affinity tryptase-specific polyclonal antibodies comprising:

a) inoculating an avian with tryptase;

b) isolating immunoglobulins from serum taken from the avian or from the yolk of eggs laid by the avian;

c) contacting the immunoglobulins to a tryptase-immobilized affinity matrix, thereby binding tryptase-specific immunoglobulins to the affinity matrix;

d) eluting non-tryptase-specific immunoglobulins from the affinity matrix;

e) eluting a first fraction of low affinity tryptase-specific antibodies from the affinity matrix by washing with a first buffered solution;

f) eluting a second fraction of high affinity tryptase-specific antibodies from the affinity matrix by washing with a second buffered solution; and g) collecting the second fraction of high affinity tryptase-specific antibodies.

2. The method of claim 1, wherein in step a) a chicken is inoculated.

3. The method of claim 1, wherein in step a) a turkey is inoculated.

4. The method of claim 1, wherein in step d) the non-tryptase-specific immunoglobulins are eluted from the affinity matrix using a buffered saline solution.

5. The method of claim 1, wherein in step e) the first fraction of low affinity tryptase-specific antibodies is eluted from the affinity matrix by washing with a first solution comprising an aqueous solution of $MgCl_2$.

6. The method of claim 5, wherein in step e) the first fraction of low affinity tryptase-specific antibodies is eluted from the affinity matrix by washing with an aqueous solution of from about 1M to about 3M $MgCl_2$.

7. The method of claim 1, wherein in step f) the second fraction of high affinity tryptase-specific antibodies is eluted from the affinity matrix by washing with an aqueous solution of glycine.

8. The method of claim 7, wherein in step f) the second fraction of high affinity tryptase-specific antibodies is eluted from the affinity column by washing with and aqueous solution of from about 0.01M to about 0.1M glycine.

9. The method of claim 1, wherein in step f) the second fraction of high affinity tryptase-specific antibodies is eluted from the affinity matrix by washing with an aqueous acidic buffered solution having a $pH \leq 3$.

10. The method of claim 1, wherein step e) further comprises collecting the first fraction of low affinity tryptase-specific antibodies.

* * * * *